(12) United States Patent
Gerlach et al.

(10) Patent No.: US 9,700,665 B2
(45) Date of Patent: Jul. 11, 2017

(54) CONTACT PROTECTION APPARATUS FOR A MEDICAL FLUID-CONDUCTING CASSETTE AND CASSETTE

(75) Inventors: Daniel Gerlach, Frankfurt (DE); Juergen Haecker, Neu-Anspach (DE); Stefan Kreber, Saarbruecken (DE); Lothar Leick, Merzig (DE); Wolfgang Schulz, Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 139 days.

(21) Appl. No.: 13/559,948

(22) Filed: Jul. 27, 2012

(65) Prior Publication Data
US 2013/0030404 A1 Jan. 31, 2013

Related U.S. Application Data

(60) Provisional application No. 61/512,952, filed on Jul. 29, 2011.

(30) Foreign Application Priority Data

Jul. 29, 2011 (DE) .......... 10 2011 108 781

(51) Int. Cl.
| | |
|---|---|
| *A61B 19/00* | (2006.01) |
| *A61M 1/36* | (2006.01) |
| *A61M 1/00* | (2006.01) |
| *A61M 37/00* | (2006.01) |
| *A61B 19/04* | (2006.01) |

(Continued)

(52) U.S. Cl.
CPC .......... *A61M 1/367* (2013.01); *A61M 1/3621* (2013.01); *A61J 1/14* (2013.01); *A61M 2205/121* (2013.01); *A61M 2205/6045* (2013.01); *A61M 2209/06* (2013.01); *F04B 43/009* (2013.01)

(58) Field of Classification Search
CPC ........ A61M 2209/084; A61M 2209/06; A61M 2205/121; A61M 2205/6045; A61M 1/3621; A61M 1/367; A61M 39/10; A61M 39/12; F04B 43/009; A61J 1/14
USPC .......................... 604/403, 29, 5.04; 206/438
See application file for complete search history.

(56) References Cited

U.S. PATENT DOCUMENTS

| | | | | |
|---|---|---|---|---|
| 4,314,025 A | * | 2/1982 | McCue ................ | A01N 1/02 210/638 |
| 5,441,636 A | * | 8/1995 | Chevallet ............ | A61M 1/16 210/232 |

(Continued)

FOREIGN PATENT DOCUMENTS

| | | |
|---|---|---|
| DE | 19814695 A1 | 10/1999 |
| DE | 19828650 A1 | 12/1999 |
| EP | 0966984 A2 | 12/1999 |

*Primary Examiner* — Tatyana Zalukaeva
*Assistant Examiner* — Andrew J Mensh
(74) *Attorney, Agent, or Firm* — Fish & Richardson P.C.

(57) ABSTRACT

The present invention relates to a contact protection apparatus for covering a connection point of a medical fluid-conducting cassette for a medical fluid treatment, having at least one covering device for covering the connection point before the use of the cassette, and having at least one connection section for detachably connecting or holding the contact protection apparatus on the cassette. The present invention further relates to a medical fluid-conducting cassette having at least one contact protection apparatus according to the present invention.

15 Claims, 4 Drawing Sheets

(51) Int. Cl.
  *A61J 1/14* (2006.01)
  *F04B 43/00* (2006.01)

(56) References Cited

U.S. PATENT DOCUMENTS

| | | |
|---|---|---|
| 2008/0093246 A1* | 4/2008 | Duchamp et al. ............ 206/438 |
| 2010/0274168 A1* | 10/2010 | Gronau .................. A61M 1/30 |
| | | 604/5.04 |
| 2011/0064608 A1 | 3/2011 | Lee et al. |
| 2011/0098635 A1* | 4/2011 | Helmore et al. ................ 604/29 |

* cited by examiner

CONTACT PROTECTION APPARATUS FOR A MEDICAL FLUID-CONDUCTING CASSETTE AND CASSETTE

CROSS REFERENCE TO RELATED APPLICATIONS

This application claims the benefit of U.S. Provisional Patent Application No. 61/512,952 filed on Jul. 29, 2011 and German Patent Application No. 10 2011 108 781.1, filed Jul. 29, 2011, both of which are herein incorporated by reference in their entireties.

FIELD OF INVENTION

The present invention relates to a contact protection apparatus for covering a connection point of a fluid-conducting cassette for a medical fluid treatment, e.g., for covering a substitute point of a blood cassette such as can be used in dialysis devices. It further relates to a medical fluid-conducting cassette.

BACKGROUND OF INVENTION

The handling of fluid-conducting cassettes, e.g., blood cassettes, by medical personnel always bears the risk that, during unpacking of a cassette from the sterile packaging, connection points which are used for adding a fluid into the cassette during the treatment of the patient (in short: fluid addition point of the cassette) are touched with the finger or an item or object by accident and thus are contaminated. Various solutions are known from practice, for example in the form of detachably adhered or strippable protective foils.

One object of the present invention is to propose a further contact protection apparatus for covering a joint or connection point of a fluid-conducting cassette for a medical fluid treatment. In addition, a medical fluid-conducting cassette is to be specified.

The contact protection apparatus according to the present invention for covering a joint or connection point of a medical fluid-conducting cassette for a medical fluid treatment comprises at least one covering device for covering the connection point before the use of the cassette, i.e., before the cassette is mounted to a fluid treatment apparatus. It further comprises at least one connection section for the detachable connection or holding of the contact protection apparatus to or on or at the cassette.

The at least one covering device of the contact protection apparatus according to the present invention is placeable over at least one connection point of a fluid-conducting cassette and wide enough to cover this or several connection points of the cassette such that with normal use of the attached contact protection device no area of the connection point can be contaminated by being touched with the fingers. The covering device may have any form known from the state of the art, e.g., it may be plate-shaped. It may be designed to be rectangular, semi-circular or the like, and so on. The size of the covering device may be chosen depending on the size of the individual connection point to be protected.

The present invention further relates to a medical fluid-conducting cassette with at least one contact protection apparatus according to the present invention.

Advantageous developments of the present invention are each also the subject of the dependent claims.

In all of the following embodiments, the use of the expression "may be" or "may have" and so on, is to be understood synonymously with "preferably is" or "preferably has", respectively, and so on, and is intended to illustrate exemplary embodiments according to the present invention.

Embodiments according to the present invention may comprise some or all of the following features in arbitrary combination.

The covering device is in some embodiments according to the present invention held on the cassette in particular exclusively by means of tension or material stiffness. In these embodiments, there is no firmly bonded connection or adhesive joint between the covering device and the cassette.

In some embodiments according to the present invention the contact protection apparatus is embodied and/or connected to be removable from the cassette without being damaged.

The contact protection apparatus is in some embodiments according to the present invention held on the cassette by means of a connection section. The connection section provides for a detachable and stable connection of the contact protection apparatus and the cassette. This connection may be done without adhesives. It may be a latching, arresting or locking, insertion, clamping, screwing, holding by means of physical force or another type of detachable connection known from the state of the art.

In some embodiments according to the present invention the contact protection apparatus is embodied to be repeatedly connectable with and detachable from the cassette.

In certain embodiments, the contact protection apparatus according to the present invention is plate-shaped. In some embodiments according to the present invention, the contact protection apparatus is one-piece or integral. However, it is recognizable for the person skilled in the art that the contact protection apparatus may both have any arbitrary form known from the state of the art in order to serve its function and be produced to be or have one or more pieces or parts.

In some embodiments according to the present invention, the contact protection apparatus is held on the cassette only by the connection section.

In some embodiments according to the present invention, the contact protection apparatus comprises at least one encoding structure for an arrangement which is encoded on the fluid-conducting cassette in relation to the shape of the contact protection apparatus. The encoded arrangement may contribute to a stable connection of the contact protection apparatus with the cassette. For this, the encoding structure has a shape which for example correlates or complements or is complementary with the shape or contour of an edge (or a different area) of the cassette. This effects on the one hand a stable connection between the contact protection apparatus and the cassette which in its edge area also proceeds in the shape of the encoding structure. Thus, the encoding structure may prevent for example shifting of the contact protection apparatus or its twisting around the axis of its connection with the cassette, for example around the connection section. On the other hand, the encoding structure may advantageously prevent mounting of the contact protection apparatus to the cassette in a position other than intended during the production process. Thus, a mounting of the contact protection apparatus which is ineffective for the intended contact protection may advantageously be prevented.

In some embodiments according to the present invention, the encoding structure of the contact protection apparatus is undulating or comprises an undulating section. It is recognizable for the person skilled in the art that the encoding structure may have any conceivable form by means of which it can fulfill at least one of the above-mentioned functions or advantages. For example, it may comprise a straight line, a zigzag pattern or any other stepped pattern. It may comprise a continuous or a non-continuous pattern, and so on.

In certain embodiments according to the present invention, the encoding structure of the contact protection apparatus is a recess provided for this purpose in at least one section or on one side of the contact protection apparatus.

In some embodiments according to the present invention, the contact protection apparatus comprises at least one fixing device for the detachable intake, delimitation or fixation of inlet and/or outlet tubes of the fluid-conducting cassette.

For this, the fixing device holds the tubes in some embodiments according to the present invention in a desired position relative to the cassette. The fixing device can thus prevent the tubes from being damaged by kinking or its contamination by unintended detachment of the tubes from the cassette.

In certain embodiments according to the present invention, the fixing device is designed to be multi-part. Between the individual sections of the multi-part fixing device, other objects such as for example tube clamps which in turn may be connected with the above-mentioned tubes may be held temporarily by means of friction or latching effect. This may serve the protection of the objects at least until the use of the cassette.

In some embodiments according to the present invention of the contact protection, the fixing device is arranged only on one side of the contact protection apparatus. It extends only on one side.

In some embodiments according to the present invention, the contact protection apparatus comprises a completely planar or exclusively planar surface. This surface faces away from the connection point during use of the contact protection apparatus. The planar surface advantageously prevents an unintended entangling of the contact protection apparatus with other objects before the use of the cassette or getting caught on these which could detach the contact protection apparatus unintentionally from the cassette.

In certain embodiments according to the present invention, the contact protection apparatus comprises at least one grip area for grasping the protection apparatus in order to detach the contact protection apparatus from the fluid-conducting cassette by hand. By means of the grip area, the user removes or detaches the contact protection apparatus from the cassette before inserting the cassette into a fluid treatment apparatus.

The grip area may have any design known from the state of the art, in particular such which facilitates or enables a non-slip holding or grasping of the grip area. For example, the grip area may be designed as a ring, studs or knobs, latch and so on or comprise a fluting or riffles or a rough surface.

In some embodiments according to the present invention of the contact protection apparatus, the covering device is not present on the grip area, but on a different section of the contact protection apparatus. This has the effect that the covering device does not have to be touched in order to detach the contact protection apparatus from the cassette. It thus minimizes the risk of unintended contamination during detachment of the contact protection apparatus.

In certain embodiments of the contact protection apparatus according to the present invention, the grip area is present on a section of the contact protection apparatus which is opposite the covering device. This may contribute to a detachment of the contact protection apparatus from the cassette without contamination.

In some embodiments according to the present invention of the medical fluid-conducting cassette, the contact protection apparatus is connected with the cassette without adhesives.

In some embodiments according to the present invention, the contact protection apparatus comprises a section which protrudes from the edge of the cassette.

In some embodiments according to the present invention, the grip area of the contact protection apparatus is arranged on the section which protrudes from the edge of the cassette, in order to facilitate the removal of the contact protection apparatus from the cassette for the user.

In certain embodiments according to the present invention of the contact protection apparatus, its connection section is introduced in at least one retaining hole or a centering hole of the cassette in order to connect the contact protection apparatus—optionally only by means of this measure—with the cassette. This retaining hole or centering hole of the cassette may be provided to be connected with a centering or retaining device of a fluid treatment apparatus. It serves to, for example, hold or center the cassette at the fluid treatment apparatus during use, for example during a dialysis treatment.

In some embodiments according to the present invention, the connection section of the contact protection apparatus during use prevents the cassette from being mounted to a fluid treatment apparatus or the cassette from being inserted herein. This is achieved for example in that when the contact protection apparatus is connected with the cassette, the connection section is stuck or plugged in the centering hole or retaining hole of the cassette. As the cassette with the attached contact protection apparatus cannot be mounted to the fluid treatment apparatus because its centering hole is not exposed, the contact protection apparatus has to be deliberately removed first.

In further embodiments according to the present invention, the contact protection apparatus is designed, for example through its dimensions or its type of connection with the cassette, such that the cassette with the attached contact protection apparatus may be mounted to the fluid treatment apparatus, however, e.g., a cover, or for example a machine door of the apparatus, cannot be closed without the contact protection apparatus having first been removed from the cassette. This also serves to ensure that the contact protection apparatus is reliably removed before the use of the cassette.

In some advantageous embodiments according to the present invention, the contact protection apparatus is sterilized together with the cassette. The sterilization process of the cassette takes place with the attached contact protection apparatus in these embodiments. This is possible according to the present invention as in such embodiments there is no firmly bonded or steam-impermeable connection between the covering device of the contact protection apparatus—in its state of being located on the connection point—and the cassette and/or the connection point. Thus, the steam permeability of the contact protection apparatus is ensured. The connection point may be successfully sterilized even with the attached contact protection apparatus or covering device, for example with hot steam.

This advantage may also arise if or when the contact protection apparatus and the cassette are made of the same material or similar materials, at least of materials which can be sterilized by means of the same sterilization process which can be used to sterilize the cassette.

In some embodiments according to the present invention, the at least one connection point which is or will be covered by means of the covering device is a joint for a substitute line.

In a further embodiment according to the present invention, the medical fluid-conducting cassette is designed as a blood cassette, for example for the dialysis treatment, in particular for hemodialysis, hemofiltration, hemodiafiltration, peritoneal dialysis, acute dialysis, and so on.

Some or all embodiments according to the present invention may comprise one, more or all of the advantages named above and/or hereafter.

Detaching the contact protection apparatus is advantageously possible without considerable application of force due to the above-mentioned embodiment of the contact protection apparatus.

In some advantageous embodiments, there is a reduced risk of unintentionally contaminating the connection point of the cassette, for example by touching it with the hand, as the grip area of the contact protection apparatus is spaced far enough from the covering device.

The contact protection apparatus is in advantageous embodiments made of the same material as the cassette. Thus, the contact protection apparatus may undergo the same sterilization processes as the cassette. In addition, it may be disposed of the same way as or together with the cassette.

Detaching the contact protection apparatus from the cassette may in advantageous embodiments be carried out with one hand.

In certain embodiments according to the present invention, the contact protection apparatus comprises accordingly soft or flexible materials or rounded edges such that a risk of injury for the user during its operation as well as the risk of damaging other parts of the contact protection apparatus or the cassette, for example by sharp contours, is minimized.

As it is possible to do without the use of adhesives for mounting the contact protection apparatus to the cassette, no residual adhesive can remain at the cassette when the contact protection apparatus is detached from the cassette and possibly get into the interior of the cassette via the connection point.

Other than, e.g., when using sterilizing caps, there is according to the present invention no risk of unintentionally touching the connection point when unpacking the cassette.

Other than as with protective foils and sterilizing caps, the contact protection apparatus according to the present invention may be attached during the sterilization of the cassette. A separate sterilization of the contact protection apparatus and the cassette with subsequent assembly is advantageously not necessary.

BRIEF DESCRIPTION OF THE DRAWINGS

The present invention is hereafter exemplarily explained by means of the appended drawings in which identical reference numerals refer to identical or similar components. In the figures it applies that.

DETAILED DESCRIPTION

Figure 1:
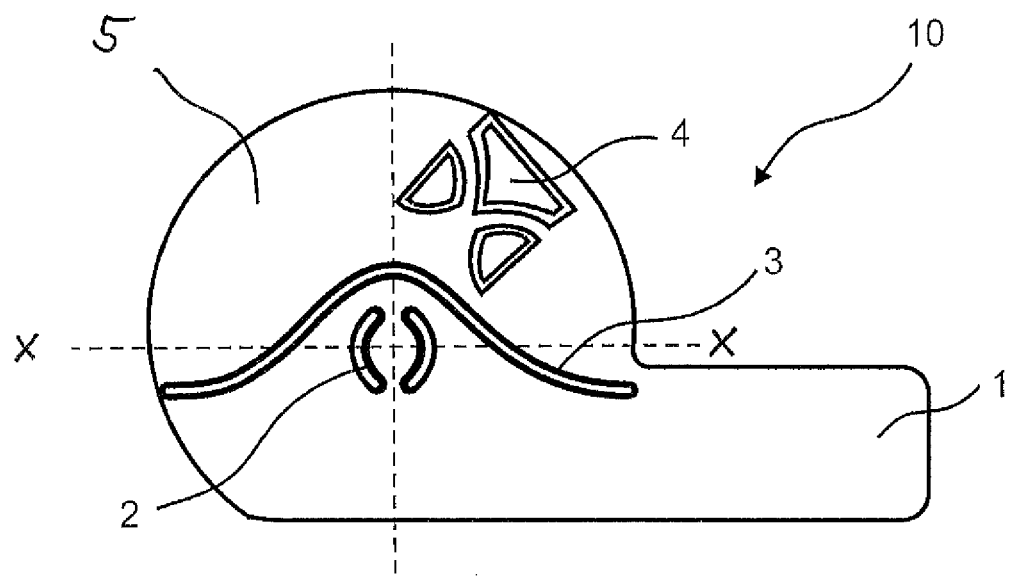
FIG. 1 shows the contact protection apparatus according to the present invention from below, with a view on its side which during use is turned towards the fluid-conducting cassette.

FIG. 1 shows a possible embodiment of the contact protection apparatus 10 according to the present invention. The contact protection apparatus 10 comprises a covering device 1, a connection section 2, an encoding structure 3, a fixing device 4 and a grip area 5.

The contact protection apparatus 10 according to the present invention is here exemplarily illustrated as an extensive plate or disc with a wider section which holds the connection section 2 for the connection of the contact protection apparatus 10, and a narrower section which during use as a covering device 1 covers a connection point 41 (see FIG. 5) which is not shown here. The covering device 1 is wide enough to completely cover the connection point 41 of a fluid-conducting cassette 60 (not shown in FIG. 1, see FIG. 5), by means of which a fluid connection may be established to the cassette. Thus, an unintended touching of the connection point 41 of the cassette 60 before its use, i.e. before mounting the cassette 60 to a fluid treatment apparatus is prevented by means of the covering device 1. Unintended touching of the connection point 41 is prevented by means of the covering device 1 even during removal of the contact protection apparatus 10.

The covering device 1 is held on the cassette 60 by means of tension or via the material stiffness of the contact protection apparatus 10. The contact protection apparatus 10 in turn is held on the cassette 60 by means of the connection section 2.

The connection section 2 provides for a detachable and stable connection of the contact protection apparatus 10 with the cassette 60. This connection is without adhesives and may be a latching, arresting or locking, insertion, clamping, screwing or another type of detachable connection known from the state of the art. The connection section 2 is in FIG. 2 plug-in connection or latching connection.

In some embodiments according to the present invention, the contact protection apparatus 10 is held on the cassette 60 only by the connection section 2, as is also shown in the figures. Between the covering device 1 and the cassette 60 there is in some embodiments according to the present invention no firmly bonded connection.

The encoding structure 3 contributes to a stable connection of the contact protection apparatus 10 with the cassette 60.

The encoding structure 3 has a shape which correlates or complements or is complementary with the shape or contour of an edge or a section of the cassette 60. The encoding structure 3 is undulating in the embodiment shown. This effects on the one hand a stable connection between the contact protection apparatus 10 and the cassette 60 which in the edge area is also undulating, i.e. it prevents for example the displacement of the contact protection apparatus 10 or its twisting around the axis of its connection with the cassette 60, here around the connection section 2. On the other hand, the encoding structure 3 prevents mounting of the contact protection apparatus 10 to the cassette 60 in a position other than intended during the production process. Thus, mounting the contact protection apparatus 10 in a way which is ineffective for the contact protection may be advantageously prevented.

The fixing device 4 of the contact protection apparatus 10 is optionally provided. It serves, if present, to detachably intake for example inlet and outlet tubes. The fixing device 4 retains the tubes in a desired position to the cassette 60. It can thus prevent damage of the tubes by kinking or their contamination by unintentional detachment of the tubes from the cassette 60.

In FIG. 1, the fixing device 4 is embodied to have three parts. Between the individual, e.g., three, sections, other objects such as tube clamps can be temporarily retained by means of friction. This may serve to protect the objects until the use of the cassette 60.

Figure 2:
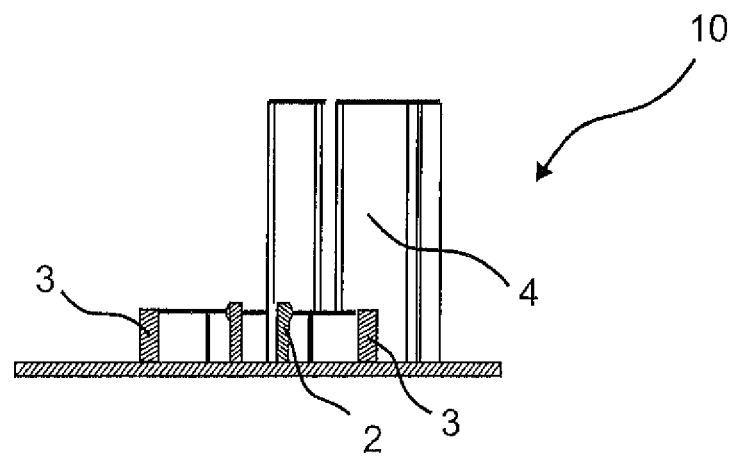
FIG. 2 shows a lateral illustration of the contact protection apparatus according to the present invention in a sectional view along the dashed line from FIG. 1.

FIG. 2 shows the contact protection apparatus 10 according to the present invention in a section along the dashed line x-x from FIG. 1 from the side. The fixing device 4 is here embodied to be spiry or tower-shaped.

In the embodiment shown here of the contact protection apparatus 10 according to the present invention, the fixing device 4 is arranged only on one side of the contact protection apparatus 10. The contact protection apparatus 10 according to the present invention comprises in the embodiment illustrated here on one side neither sections of the connection section 2, of the encoding structure 3 nor of the fixing device 4. In some embodiments according to the present invention, the contact protection apparatus 10 comprises on one side (top or bottom) no prominent structures at all.

Figure 3:
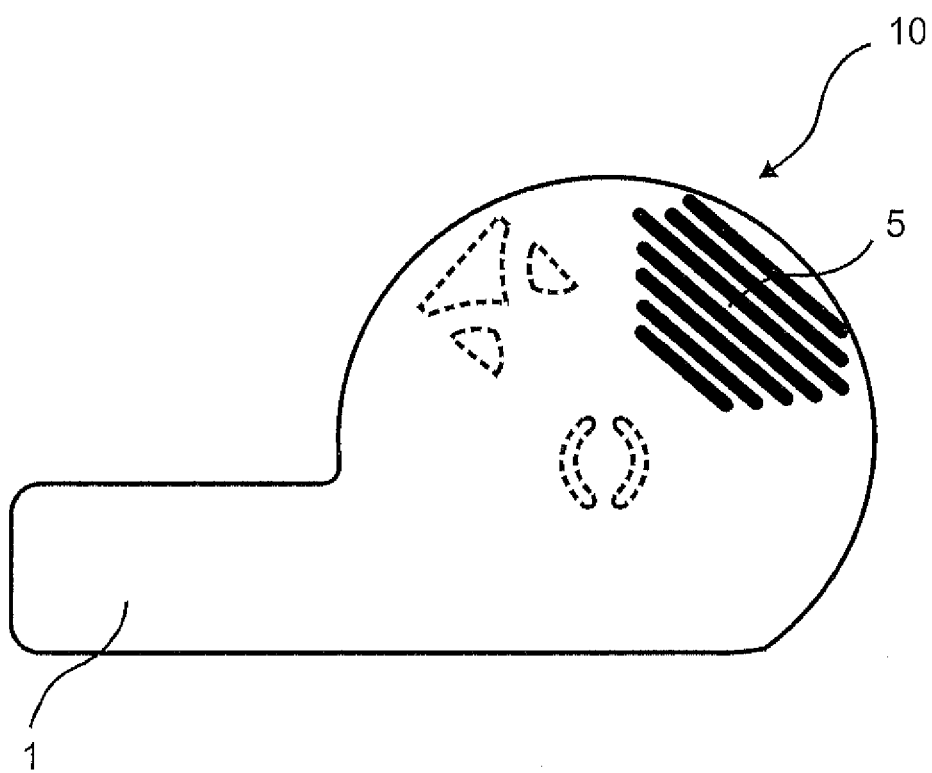
FIG. 3 shows a top view on the contact protection apparatus according to the present invention of FIG. 1, on its side which is facing away from the fluid-conducting cassette during use.

FIG. 3 shows the contact protection apparatus 10 according to the present invention of FIGS. 1 and 2 from above or in a top view. On this side of the contact protection apparatus 10, a riffled surface of the grip area 5 is arranged. The grip area 5 thus comprises a structure or surface structure which enables a non-slip retaining of the grip area, for example as a ring, studs, latches etc. The grip area 5 may have any design known from the state of the art for its better grasping. Such a design or surface structure is, however, again only optionally provided.

By means of the grip area 5, the user removes or detaches the contact protection apparatus 10 from the cassette 60 before inserting the cassette into a fluid treatment apparatus.

The connection section 2 and the fixing device 4 are only indicated with dashed lines. These do not extend to the side of the contact protection apparatus 10 which is considered in FIG. 3.

Figure 4:
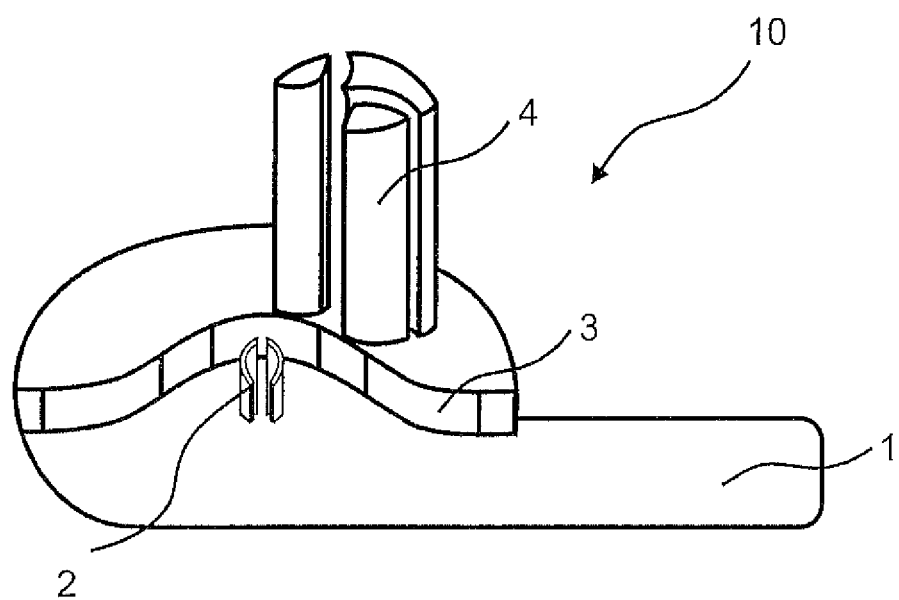
FIG. 4 shows the contact protection apparatus according to the present invention of the preceding figures in a perspective view with view on the bottom shown in FIG. 1.

FIG. 4 shows a perspective illustration of the contact protection apparatus 10 according to the present invention with a view on its side which during use is turned towards a cassette 60.

Figure 5:
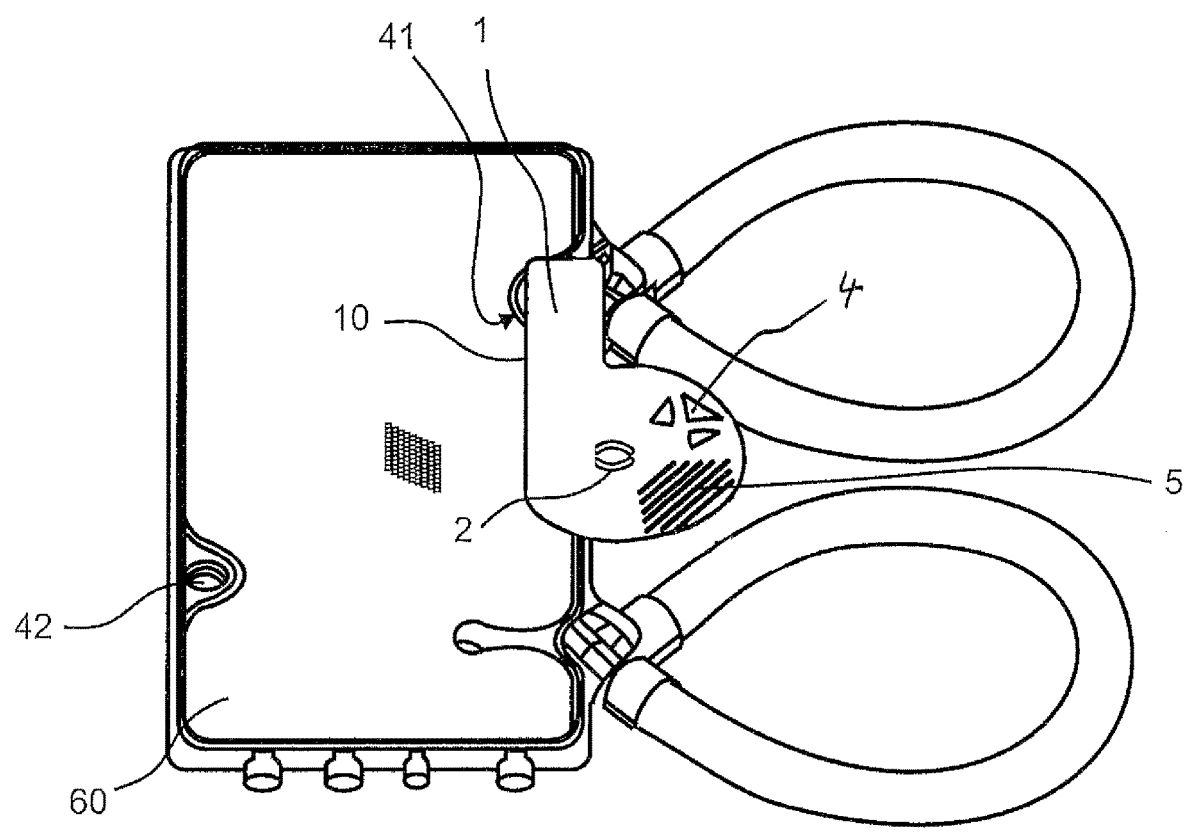
FIG. 5 shows a perspective illustration of the contact protection apparatus according to the present invention of the preceding figures during use on a fluid-conducting cassette.

FIG. 5 shows in a perspective illustration the contact protection apparatus 10 according to the present invention of the preceding figures, connected with a cassette 60.

A possible embodiment of the contact protection apparatus 10 comprises, as illustrated, a plate-shaped covering device 1 which covers exactly one connection point 41 completely. In other embodiments according to the present invention, the contact protection apparatus is for example T-shaped and covers two or more connection points at the same time. Also arbitrary shapes other than the one shown here are provided according to the present invention.

When or if the contact protection apparatus 10 is connected with the cassette 60, as is shown in FIG. 5, the connection section 2 which is only outlined in FIG. 5 for example plugs into a centering hole or retaining hole not shown here of the cassette 60, provided for its centering or retaining in a fluid treatment apparatus (an opening 42 of this kind which is not connected with the contact protection apparatus 10 is shown at the left edge of the cassette 60). The cassette 60 cannot be mounted to the fluid treatment apparatus in this state as the centering hole is not freely accessible. As, however, a free access to the centering hole is a prerequisite for mounting the cassette 60 to the fluid treatment apparatus, the contact protection apparatus 10 has to be deliberately removed.

The contact protection apparatus 10 may also be designed, for example through its dimensions or its type of connection with the cassette 60, such that the cassette 60 with attached protection apparatus 10 may be mounted to the fluid treatment apparatus, however, e.g., the door of the apparatus may not be closed before the contact protection apparatus 10 is detached from the cassette 60. This also serves to ensure that the contact protection apparatus 10 is or was reliably removed before the use of the cassette 60.

Detaching the contact protection apparatus 10 takes place without considerable application of force. It further takes place with a reduced risk of unintentional contamination of the connection point 41 of the cassette 60, for example by touching it with the hand, as the grip area 5 of the contact protection apparatus 10 is spaced from the covering device 1.

Further, the grip area 5 protrudes from the edge of the cassette 60 in order to facilitate the removal of the contact protection apparatus 10 for the user.

What is claimed is:

1. A blood cassette assembly for use with a fluid treatment apparatus to perform a medical fluid treatment, the blood cassette assembly comprising:
   a blood cassette comprising:
      a housing defining fluid-conducting interior space and a hole for releasably coupling with the fluid treatment apparatus while the blood cassette and the fluid treatment apparatus perform the medical fluid treatment; and
      a connector, coupled to the housing, for releasably connecting a fluid flow line to the blood cassette to facilitate fluid flow between the fluid flow line and the fluid-conducting interior space while the blood cassette and the fluid treatment apparatus perform the medical fluid treatment; and
   a cassette protection device releasably coupled to the blood cassette and comprising:
      a cover plate; and
      a connection section coupled to and projecting from the cover plate, the connection section releasably coupled with the hole such that the cover plate covers the connector,
   wherein the blood cassette is operable with the fluid treatment apparatus to perform the medical fluid treatment while the cassette protection device is uncoupled from the blood cassette, and wherein the blood cassette is inoperable with the fluid treatment apparatus to perform the medical fluid treatment while the cassette protection device is coupled to the blood cassette.

2. The blood cassette assembly according to claim 1, wherein the cassette protection device includes at least one encoding structure that is shaped in correspondence to a shape of the blood cassette.

3. The blood cassette assembly according to claim 1, wherein the cassette protection device includes at least one fixing device for detachable intaking or retaining at least one of inlet or outlet tubes of the blood cassette.

4. The blood cassette assembly according to claim 3, wherein the fixing device is arranged only on one side of the cassette protection device.

5. The blood cassette assembly according to claim 1, wherein the cover plate includes a grip area.

6. The blood cassette assembly according to claim 1, wherein the cassette protection device is a single piece.

7. The blood cassette assembly according to claim 1, wherein the cassette protection device is coupled to the blood cassette without adhesives.

8. The blood cassette assembly according to claim 1, wherein the cassette protection device comprises a section which protrudes from an edge of the blood cassette while the cassette protection device is coupled to the blood cassette.

9. The blood cassette assembly according to claim 8, wherein the grip area of cassette protection device is arranged on the section which protrudes from the edge of the blood cassette while the cassette protection device is coupled to the blood cassette.

10. The blood cassette assembly according to claim 1, wherein the connection section of the cassette protection device mechanically prevents the blood cassette from being operably mounted to the fluid treatment apparatus.

11. The blood cassette assembly according to claim 1, wherein the connection section of the cassette protection device comprises a latching connection.

12. The blood cassette assembly according to claim 1, wherein the cassette protection device is or was sterilized together with the blood cassette.

13. The blood cassette assembly according to claim 12, wherein there is no firmly bonded connection between the cover plate of the cassette protection device and the blood cassette or the connector when the cover plate covers the connector.

14. The blood cassette assembly according to claim 2, wherein the blood cassette includes an edge contour that is shaped in correspondence to a contour of the at least one encoding structure.

15. The blood cassette assembly according to claim 1, wherein the connector is adapted for connecting a substituate line to the blood cassette.

* * * * *

UNITED STATES PATENT AND TRADEMARK OFFICE
CERTIFICATE OF CORRECTION

PATENT NO. : 9,700,665 B2  
APPLICATION NO. : 13/559948  
DATED : July 11, 2017  
INVENTOR(S) : Daniel Gerlach et al.

It is certified that error appears in the above-identified patent and that said Letters Patent is hereby corrected as shown below:

On the Title Page

(75) Inventors, Column 1, Line 5, delete "Wendel" and insert --St. Wendel--.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*